(12) United States Patent
Craig et al.

(10) Patent No.: US 9,050,252 B2
(45) Date of Patent: Jun. 9, 2015

(54) METHOD OF SURFACE TREATING INORGANIC OXIDE PARTICLES, HARDENABLE DENTAL COMPOSITIONS, SURFACE TREATED PARTICLES, AND SURFACE TREATMENT COMPOUNDS

(75) Inventors: Bradley D. Craig, Lake Elmo, MN (US); Ahmed S. Abuelyaman, Woodbury, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 128 days.

(21) Appl. No.: 13/695,443

(22) PCT Filed: May 6, 2011

(86) PCT No.: PCT/US2011/035461
§ 371 (c)(1),
(2), (4) Date: Oct. 31, 2012

(87) PCT Pub. No.: WO2011/149631
PCT Pub. Date: Dec. 1, 2011

(65) Prior Publication Data
US 2013/0059941 A1    Mar. 7, 2013

Related U.S. Application Data

(60) Provisional application No. 61/347,967, filed on May 25, 2010.

(51) Int. Cl.
*A61K 6/083* (2006.01)
*A61K 6/00* (2006.01)
*A61K 6/09* (2006.01)

(52) U.S. Cl.
CPC ............... *A61K 6/083* (2013.01); *A61K 6/0023* (2013.01); *A61K 6/007* (2013.01); *A61K 6/09* (2013.01)

(58) Field of Classification Search
USPC .......................................... 523/116, 202, 212
See application file for complete search history.

(56) References Cited

U.S. PATENT DOCUMENTS

| | | | |
|---|---|---|---|
| 4,503,169 A | | 3/1985 | Randklev |
| 4,650,889 A | * | 3/1987 | Plueddemann ............... 556/421 |
| 5,130,347 A | | 7/1992 | Mitra |
| 5,154,762 A | | 10/1992 | Mitra |
| 5,501,727 A | | 3/1996 | Wang |
| 5,545,676 A | | 8/1996 | Palazzotto |
| 5,962,550 A | | 10/1999 | Akahane |
| 6,126,922 A | | 10/2000 | Rozzi |
| 6,284,898 B1 | | 9/2001 | Moszner |
| 6,387,981 B1 | | 5/2002 | Zhang |
| 6,399,693 B1 | * | 6/2002 | Brennan et al. ............... 524/494 |
| 6,572,693 B1 | | 6/2003 | Wu |
| 6,730,156 B1 | | 5/2004 | Windisch |
| 6,794,520 B1 | | 9/2004 | Moszner |
| 6,899,948 B2 | | 5/2005 | Zhang |
| 7,090,721 B2 | | 8/2006 | Craig |
| 7,090,722 B2 | | 8/2006 | Budd |
| 7,091,259 B2 | * | 8/2006 | Bui et al. ...................... 523/115 |
| 7,156,911 B2 | | 1/2007 | Kangas |
| 7,241,437 B2 | | 7/2007 | Davidson |
| 7,649,029 B2 | | 1/2010 | Kolb |
| 7,674,850 B2 | | 3/2010 | Karim |
| 2004/0249037 A1 | * | 12/2004 | Kolbe et al. .................. 524/401 |
| 2005/0252413 A1 | | 11/2005 | Kangas |
| 2006/0004121 A1 | | 1/2006 | Ding |
| 2008/0237907 A1 | | 10/2008 | Klee |
| 2008/0287562 A1 | | 11/2008 | Frances |
| 2009/0032989 A1 | | 2/2009 | Karim |
| 2009/0088494 A1 | | 4/2009 | Luchterhandt |
| 2009/0111904 A1 | | 4/2009 | Odaka |
| 2009/0194722 A1 | | 8/2009 | Tiberghien |
| 2009/0247665 A1 | | 10/2009 | Thalacker |

FOREIGN PATENT DOCUMENTS

| | | |
|---|---|---|
| EP | 0319829 | 6/1989 |
| EP | 2008636 | 12/2008 |
| JP | 60-123478 | 7/1985 |
| JP | 2001-39956 | 2/2001 |
| WO | WO 01/30305 | 5/2001 |
| WO | WO 01/30307 | 5/2001 |
| WO | WO 03/015720 | 2/2003 |
| WO | WO 03/063804 | 8/2003 |
| WO | WO 2006/122081 | 11/2006 |
| WO | WO 2008/082881 | 7/2008 |
| WO | WO 2010/045105 | 4/2010 |
| WO | WO 2010/074862 | 7/2010 |
| WO | WO 2011/126647 | 10/2011 |

OTHER PUBLICATIONS

Mahmoodian et al., "Synthesis of organic-inorganic hybrid compounds based on Bis-GMA and its sol-gel behavior analysis using Taguchi method", Dental Materials 24 (2008) 514-521.
Matijevic, Surface & Colloid Science, vol. 6, (1973), 23-29.
Watts et al., "Determination of Polymerization Shrinkage Kinetics in Visible-Light Cured Materials: Methods of Development", Dental Materials, Oct. 1991, pp. 281-286.
International Search Report PCT/US2011/035461 Sep. 19, 2012, 4 pgs.

* cited by examiner

*Primary Examiner* — Tae H Yoon
(74) *Attorney, Agent, or Firm* — Carolyn A. Fischer

(57) ABSTRACT

Presently described are methods of surface treating inorganic oxide particles, hardenable (e.g. dental) compositions comprising a polymerizable resin composition and surface treated particles, as well as surface treated (e.g. nanocluster) inorganic oxide particles, and silane surface treatment compounds. In one embodiment, the method comprises forming a surface treatment compound by reacting a first functional group of a (meth)acrylate monomer having a molecular weight of at least 350 g/mole with a second functional group of a silane compound wherein the first and second functional group react to form a covalent bond; and combining the surface treatment compound with inorganic oxide particles.

18 Claims, No Drawings

METHOD OF SURFACE TREATING INORGANIC OXIDE PARTICLES, HARDENABLE DENTAL COMPOSITIONS, SURFACE TREATED PARTICLES, AND SURFACE TREATMENT COMPOUNDS

SUMMARY

In one embodiment, a method of surface treating inorganic oxide particles is described. The method comprises forming a surface treatment compound by reacting a first functional group of a (meth)acrylate monomer having a molecular weight of at least 350 g/mole with a second functional group of a silane compound wherein the first and second functional group react to form a covalent bond; and combining the surface treatment compound with inorganic oxide particles. The method may further comprise drying the surface treated inorganic oxide particles to a free-flowing powder.

In another embodiment, hardenable dental compositions are described comprising a polymerizable resin composition and surface treated inorganic particles, as described herein. In a favored embodiment, the polymerizable resin composition comprises at least wt-% of a (meth)acrylate monomer having a molecular weight of at least 550 g/mole and inorganic oxide particles comprising a silane surface treatment compound derived from a (meth)acrylate monomer having a molecular weight of at least 350 g/mole.

In another embodiment, surface treated inorganic oxides particles are described wherein the particles comprise nanoclusters. The surface treatment compound comprises a silane compound derived from a (meth)acrylate monomer having a molecular weight of at least 350 g/mole and one or more (meth)acrylate groups.

In another embodiment, silane surface treatment compound(s) and surface treated inorganic oxide particles are described.

DETAILED DESCRIPTION

As used herein, "dental composition" refers to an unfilled material (i.e. total dental composition except for filler) or filled material (e.g., a dental cement or restoration) capable of adhering or being bonded to an oral surface. A curable dental composition can be used to bond a dental article to a tooth structure, form a coating (e.g., a sealant or varnish) on a tooth surface, be used as a restorative that is placed directly into the mouth and cured in-situ, or alternatively be used to fabricate a prosthesis outside the mouth and subsequently adhered in placed in the mouth.

Curable dental compositions include, for example, adhesives (e.g., dental and/or orthodontic adhesives), cements (e.g., resin-modified glass ionomer cements, and/or orthodontic cements), primers (e.g., orthodontic primers), liners (applied to the base of a cavity to reduce tooth sensitivity), coatings such as sealants (e.g., pit and fissure), and varnishes; and resin restoratives (also referred to as direct composites) such as dental fillings, as well as crowns and bridges. Highly filled dental compositions are also used for mill blanks, from which a crown may be milled. A composite is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

As used herein, "dental article" refers to an article that can be adhered (e.g., bonded) to a tooth structure. Dental articles include, for example, crowns, bridges, veneers, inlays, onlays, fillings, orthodontic appliances and devices.

As used herein, an "oral surface" refers to a soft or hard surface in the oral environment. Hard surfaces typically include tooth structure including, for example, natural and artificial tooth surfaces, bone, and the like.

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, "hardener" refers to something that initiates hardening of a resin. A hardener may include, for example, a polymerization initiator system, a photoinitiator system, a thermal initiator and/or a redox initiator system.

As used herein, the term "(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

Presently described are methods of surface treating inorganic oxide particles, hardenable (e.g. dental) compositions comprising a polymerizable resin composition and surface treated particles, as well as surface treated (e.g. nanocluster) inorganic oxide particles, and silane surface treatment compounds.

The method of surface treating inorganic oxide particles, such as nanoclusters, comprises forming a surface treatment compound by reacting a first functional (e.g. —OH) group of the (meth)acrylate monomer with a second functional (e.g. —NCO) group of a silane compound and combining the surface treatment compound with inorganic oxide particles. The surface treatment compound is formed from a (meth) acrylate monomer having a calculated molecular weight of at least 350 g/mole. Such (meth)acrylate monomer surface treatment precursor is preferably a low volume shrinkage monomer. Further, the polymerizable resin composition of the hardenable dental composition also preferably comprises one or more low volume shrinkage monomer(s) alone or in combination with other conventional (meth)acrylate monomers. In some embodiments, the surface treatment compound is formed from the same low volume shrinkage (meth)acrylate monomer(s) as the polymerizable resin composition of the hardenable (e.g. dental) composition.

The use of a higher molecular weight surface treatment, and especially a surface treatment compound derived from a low volume shrinkage monomer can reduce the polymerization shrinkage of a (e.g. filled) hardenable dental composition. The polymerization shrinkage can be determined via various methods such as Watts Shrinkage that measure the volumetric change after curing. Preferred low volume shrinkage (e.g. filled) dental compositions (useful for restorations such as fillings and crowns) described herein typically exhibit a Watts Shrinkage of less than about 2%. Watts Shrinkage can also be expressed with regard to the difference relative to a control. It has been shown that Watts Shrinkage relative to a control (using a conventional 3-methacryloxypropyltrimethoxysilane surface treatment compound) can decrease the Watts Shrinkage by least 0.10%, 0.15%, 0.20%, 0.25%, or 0.30%, by use of the surface treated filler described herein.

The (e.g. filled) dental composite materials typically exhibit sufficient diametral tensile strength (DTS) of at least about 65, 70, 75, or 80 MPa, in combination with the low Watts Shrinkage.

Several low volume shrinkage monomers and dental compositions comprising such low volume shrinkage monomers have been described in the art. Exemplary classes of compounds include branched multi(meth)acrylate monomers such as described in WO2008/08288 and multi(meth)acrylate isocyanurate compounds, such as described in EP2008636 and U.S. Provisional Application No. 61/319,534, filed Mar. 31, 2010. Other classes of low volume shrinkage monomers include (meth)acrylate monomers having a cyclic (e.g. allylic) sulfide moiety, such as described in US2008/0194722; methylene dithiepane silanes as described in U.S. Pat. No. 6,794,520; and oxetane silanes such as described in U.S. Pat. No. 6,284,898.

Low volume shrinkage monomer(s), for use as a precursor of the surface treatment compound, comprise at least one and preferable more the one (meth)acrylate group. In some embodiments, the surface treatment compound is derived from a di-(meth)acrylate monomer. In other embodiments, the surface treatment compound is derived from a (meth)acrylate monomer having at least three (meth)acrylate groups.

The low volume shrinkage monomer(s) for use as a precursor of the surface treatment compound further comprise a first functional group that can react with a second functional group of a silane compound. The first functional group of the (meth)acrylate monomer and the second functional group of the silane compound are not free-radically polymerizable (meth)acrylate groups. The first and second functional group react to form a covalent bond such as a urethane, urea, or amide linkage. For example, when the first functional group of the (meth)acrylate monomer is a hydroxyl group and the second functional group of the silane compound is an isocyanate group, a urethane linkage is formed. In yet another embodiment, when an isocyanate functional group is reacted with a amine group, a urea linkage is formed. Amides are commonly formed via reactions of a carboxylic acid with an amine. Since the (meth)acrylate groups of the surface treatment precursor monomer are not reacted during the formation of the surface treatment compound, the totality of the (meth) acrylate groups of the monomer are available to copolymerize during the hardening of the dental composition.

In some embodiments, the multi-(meth)acrylate monomer from which the surface treatment compound is derived is a bisphenol A monomer such as 2,2-bis[4-(2-hydroxy-3-methacryloyloxypropoxy)phenyl]propane (BisGMA). A representative structure for BisGMA is depicted as follows, having a (i.e. calculated) molecular weight of about 512 g/mole:

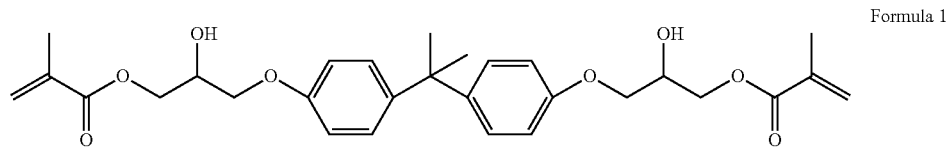 [SMILES: C=C(C)C(=O)OCC(O)COc1ccc(C(C)(C)c2ccc(OCC(O)COC(=O)C(=C)C)cc2)cc1]

Formula 1

In some embodiments, the multi-(meth)acrylate monomer from which the surface treatment compound is derived is a low volume shrinkage monomer having a calculated molecular weight greater than BisGMA, i.e. at least 550 g/mole or 600 g/mole. Higher molecular weight monomers, such as branched monomers and those containing a cyclic structure can provide lower Watts Shrinkage as compared to BisGMA. In some embodiments, the molecular weight of the low volume shrinkage monomer is at least 650 g/mole, or at least 700 g/mole, or at least 750 g/mole. In some embodiments, the molecular weight of the low volume shrinkage monomer is no greater than about 2000 g/mole, or 1500 g/mole, or 1400 g/mole, or 1300 g/mole or 1200 g/mole.

One preferred class of low volume shrinkage monomers includes branched multi(meth)acrylate monomers (e.g. having pendant (meth)acrylate moieties) such as described in WO2008/08288; incorporated herein by reference. These branched multi(meth)acrylate monomer may have the general formula

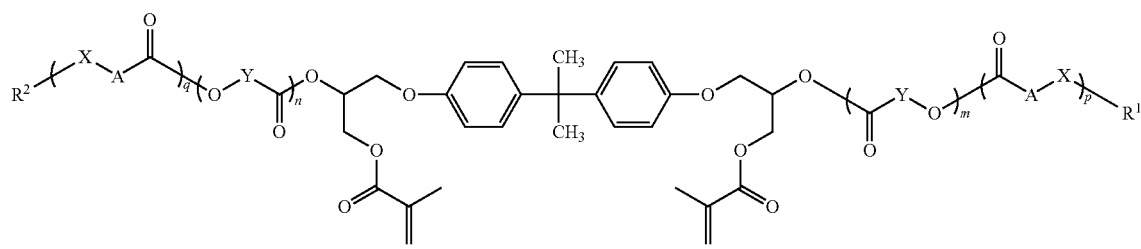

Formula 2 wherein: each X independently represents an oxygen atom (O) or a nitrogen atom (N); Y and A each independently represent an organic group, and $R^1$ represents —C(O)C(CH$_3$)═CH$_2$, and/or (ii) q=0 and $R^2$ represents —C(O)C(CH$_3$)═CH$_2$; m=1 to 5; n=0 to 5; p and q are independently 0 or 1; and $R^1$ and $R^2$ each independently represent H, —C(O)CH=CH$_2$, or —C(O)C(CH$_3$)=CH$_2$. In some embodiments, such as described in WO2008/08288, Y does not represent —NHCH$_2$CH$_2$— if (i) p=0. In favored embodiments, at least one $R^1$ or $R^2$ is —C(O)CH=CH$_2$, or —C(O)C(CH$_3$)=CH$_2$.

For embodiments wherein such branched multi(meth)acrylate monomer is utilized as a precursor to the surface treatment compound, the multi(meth)acrylate monomer further comprises a first functional group (such as —OH) that covalently bonds with a second functional group (such as —NCO) of a silane compound. The organic group(s) Y and/or A typically comprise the first functional group. Alternatively, when X is nitrogen, X may comprise the first functional group.

Some suitable low volume shrinkage urethane(meth)acrylate monomers are described in EP2008636.

In other embodiments, the surface treatment compound may be free monomer(s) derived from bisphenol A. For example, the low volume shrinkage monomer may be a di- or tri-(meth)acrylate isocyanurate monomer.

Such (meth)acrylate monomers may have the general structure

Formula 3

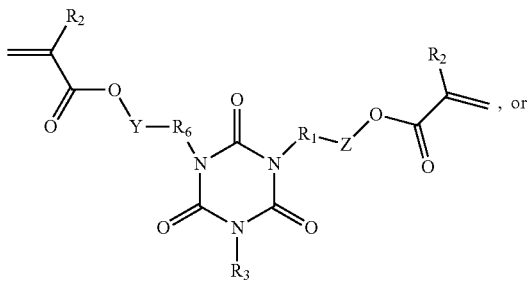

, or

Formula 4

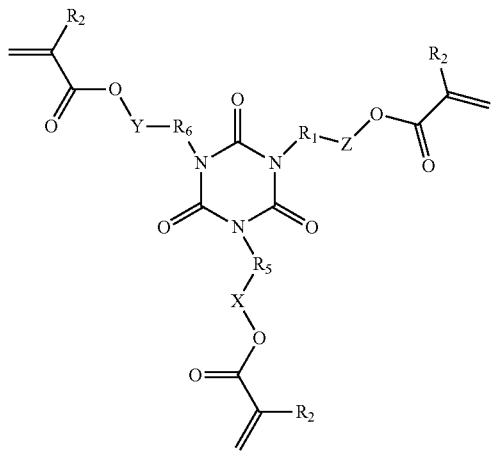

wherein
$R_1$, $R_5$, and $R_6$ are independently alkylene, arylene, or alkarylene, optionally including a heteroatom (e.g. oxygen, nitrogen, or sulfur);
$R_2$ is hydrogen or methyl; X, Y, and Z are independently alkylene, arylene, or alkarylene linking groups, comprising a heteroatom;
$R_3$ is independently hydrogen, alkyl, aryl, or alkaryl, optionally including a heteroatom; and
$R_2$ is hydrogen or methyl.

For embodiments wherein such multi(meth)acrylate isocyanurate monomer is utilized as a surface treatment compound precursor, at least one of $R_1$, $R_3$, $R_5$, $R_6$, X, Y, and Z comprises a first functional group that covalently bonds with a second functional group of a silane compound.

In one favored embodiment X, Y, and Z are independently alkylene, arylene, or alkarylene linking groups comprising at least one moiety selected from ester, thioester, ether, thioether, or combinations of such moieties; as described in 66124; incorporated herein by reference. Ester linkages can typically provide lower viscosity relative to isocyanurate monomers comprising urethane linkages.

The (meth)acrylate monomer of the surface treatment precursor, comprising the first functional group, is reacted with a second functional group of a silane compound. Various functional silane compounds are known. Such silane compounds are typically monofunctional, having a single functional group at one terminus and a silane (e.g. silanol) at the other terminus.

In one embodiment, the surface treatment compound is formed wherein a urethane linkage is formed by the reaction of the first functional group of a (meth)acrylate monomer and second functional group of a silane compound. As exemplified in the forthcoming examples, a hydroxyl functional (meth)acrylate monomer can be reacted with an isocyanate-functional silane such as 3-isocyantopropyltriethoxy silane, commercially available from Sigma-Aldrich.

Alternatively, a hydroxyl functional silane compound can be reacted with an isocyanate functional (meth)acrylate monomer.

Silanes with a hydroxyl functional group include for example bis(2-hydroxyethyl)-3-aminopropyltriethoxysilane; N-(hydroxyethyl)-N-methylaminopropyltrimethoxysilane; hydroxymethyltriethoxysilane; N-triethoxysilylpropyl)-O-polyethylene oxide urethane; N-(3-triethoxysilylpropyl)-4-hydroxybutyramide.

Isocyanate functional (meth)acrylate monomer can be formed by prereacting a diisocyanate with a hydroxyl functional (meth)acrylate monomer.

In other embodiments, the surface treatment compound is formed by reacting a first functional group of a (meth)acrylate monomer with a second functional group of silane to form a urea or amide linkage.

Monoamine functional silanes include for example 3-aminopropyltriethoxysilane; 3-aminopropyltrimethoxysilane; 4-aminobutyltriethoxysilane; 4-aminobutyltrimethoxysilane; aminophenyltrimethoxysilane (para, meta or their mixtures); 3-aminopropyltris(methoxyethoxyethoxy)silane; 3-(m-aminophenoxy)propyltrimethoxysilane); aminopropylsilanetriol; 3-aminopropylmethyldiethoxysilane; and 3-aminopropyldiisopropylethoxysilane; 3-aminopropyldimethylethylethoxysilane.

The molecular weight of the silane surface treatment derived from the (meth)acrylate monomer is greater than the (meth)acrylate monomer by a factor of the molecular weight of the silane compound precursor multiplied up to the number of first functional groups of the (meth)acrylate monomer. In some embodiments, the surface treatment does not have a significantly higher molecular weight than the (meth)acrylate monomer precursor from which is was formed. For examples, the silane surface treatment may have a molecular weight 200 g/mole to 300 g/mole greater than the (meth)acrylate monomer precursor form which it was formed. The silane surface treatment typically has a branched structure as a result of the functional group being present as pendant groups along the main chain of the (meth)acrylate monomer precursor, rather than being present as a terminal functional group(s). The molecular weight of the silane surface treatment is typically at least 600 g/mole, or 700 g/mole, or 800 g/mole, or 900 g/mole, or 1000 g/mole. In molecular weight of the surface treatment is typically no greater than 5000 g/mole. The molecular weight of the surface treatment is typically no greater than 3000 g/mole, 2500 g/mole, or 2000 g/mole, particularly for highly filled dental compositions.

The surface modification method is typically sequential comprising first preparing the surface treatment compound followed by combining the surface treatment compound with the inorganic oxide particles. Thus, the surface treatment compound is formed and then combined with inorganic particles, such as nanoclusters. The surface treated inorganic oxide (e.g. nanocluster) particles are then combined with the polymerizable resin of the dental composition. One of ordinary skill in the art appreciates that (i.e. unmodified) inorganic particles generally do not disperse well in a polymerizable resin in the absence of a surface treatment. Inorganic oxide particles typically have hydroxyl functionality on the particle surface. Thus, combining such particles concurrently with a mixture of the isocyanate silane compound and (meth)acrylate monomer (having a first functional group) results in a significant fraction of the isocyanate compound reacting directly with the particle surface.

The required amount of surface modifier is dependant upon several factors such as particle size, particle type, modifier molecular wt, and modifier type. In general it is preferred that approximately a monolayer of modifier is attached to the surface of the particle.

In some embodiments, a combination of surface modifying agents can be useful, wherein the second compound of the surface treatment compound also has a functional group co-polymerizable with a hardenable resin. Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Such silane compounds typically have a molecular weight of less than 350 g/mole or less than 300 g/mole. Preferred coupling agents include gamma-methacryloxypropyltrimethoxysilane, gamma-mercaptopropyl-triethoxysilane, gamma-aminopropyltrimethoxysilane, and the like.

Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

In some embodiments, the weight ratio of the (i.e. first) surface treatment compound comprising a (meth)acrylate monomer having a molecular weight of at least 350 g/mole covalently bonded to a compound comprising a terminal silane moiety to second surface treatment compound is at least 1:1 or at least 2:1. In some embodiments, the weight ratio of the first compound to second compound ranges up to 3:1, or 4:1, or 5:1, or 6:1, or 7:1, or 8:1 or 9:1. The inclusion of the second surface treatment compound may provide improved mechanical properties such as the diametral tensile strength The polymerizable resin of the hardenable dental composition described herein comprises one or more low volume shrinkage monomer, such as a branched multi(meth)acrylate monomer of Formula 2, as previously described; and/or a multi(meth)acrylate isocyanurate compound of Formulas 3 or 4, as previously described.

Alternatively or in addition thereto, the polymerizable resin may comprise another class of (e.g. monofunctional) low volume shrinkage (meth)acrylate monomers having a cyclic (e.g. allylic sulfide) moiety, as described in US2008/0194722; incorporated herein by reference.

Such a polymerizable compound is referred to as a hybrid monomer or a hybrid compound. The cyclic allylic sulfide moiety typically comprises at least one 7- or 8-membered ring that has two heteroatoms in the ring, one of which is sulfur. Most typically both of the heteroatoms are sulfur, which may optionally be present as part of an SO, $SO_2$, or S—S moiety. In other embodiments, the ring may comprise a sulfur atom plus a second, different heteroatom in the ring, such as oxygen or nitrogen. In addition, the cyclic allylic moiety may comprise multiple ring structures, i.e. may have two or more cyclic allylic sulfide moieties. The (meth)acryloyl moiety is preferably a (meth)acryloyloxy or a (meth)acryloylamido moiety.

In one embodiment, the other low volume shrinkage monomer includes those represented by the formulae:

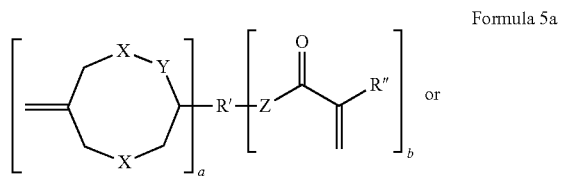

Formula 5a

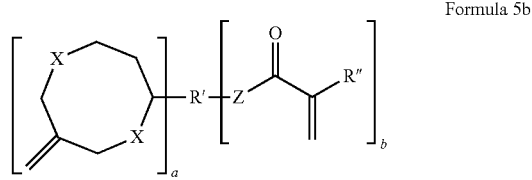

Formula 5b

In the above formulae, each X can be independently selected from S, O, N, C (e.g., $CH_2$ or CRR, where each R is independently a H or an organic group), SO, $SO_2$, N-alkyl, N-acyl, NH, N-aryl, carboxyl or carbonyl group, provided that at least one X is S or a group comprising S. Preferably, each X is S.

Y is either alkylene (e.g., methylene, ethylene, etc.) optionally including a heteroatom, carbonyl, or acyl; or is absent, thereby indicating the size of the ring, typically 7- to 10-membered rings, however larger rings are also contemplated. Preferably, the ring is either a 7- or 8-membered ring with Y thus being either absent or methylene, respectively. In some embodiments, Y is either absent or is a C1 to C3 alkylene, optionally including a heteroatom, carbonyl, acyl, or combinations thereof.

Z is O, NH, N-alkyl (straight chain or branched), or N-aryl (phenyl or substituted phenyl).

The R' group represents a linker selected from alkylene (typically having more than one carbon atom, i.e. excluding methylene), alkylene optionally including a heteroatom (e.g., O, N, S, S—S, SO, SO2), arylene, cycloaliphatic, carbonyl, siloxane, amido (—CO—NH—), acyl (—CO—O—), urethane (—O—CO—NH—), and urea (—NH—CO—NH—) groups, and combinations thereof. In certain embodiments, R' comprises an alkylene group, typically a methylene or longer group, that may be either straight chain or branched, and which can be either unsubstituted, or substituted with aryl, cycloalkyl, halogen, nitrile, alkoxy, alkylamino, dialkylamino, alkylthio, carbonyl, acyl, acyloxy, amido, urethane group, urea group, a cyclic allylic sulfide moiety, or combinations thereof.

R" is selected from H, and CH$_3$, and "a" and "b" are independently 1 to 3.

Optionally the cyclic allylic sulfide moiety can further be substituted on the ring with one or more groups selected from straight or branched chain alkyl, aryl, cycloalkyl, halogen, nitrile, alkoxy, alkylamino, dialkylamino, alkylthio, carbonyl, acyl, acyloxy, amido, urethane group, and urea group. Preferably the selected substituents do not interfere with the hardening reaction. Preferred are cyclic allylic sulfide structures that comprise unsubstituted methylene members.

A typical low volume shrinkage monomer can comprise an 8-membered cyclic allylic sulfide moiety with two sulfur atoms in the ring and with the linker attached directly to the 3-position of the ring with an acyl group (i.e., Ring-OC(O)—). Typically the weight average molecular weight (MW) of the hybrid monomer ranges from about 400 to about 900 and in some embodiments is at least 250, more typically at least 500, and most typically at least 800.

Representative polymerizable compounds having at least one cyclic allylic sulfide moiety with at least one (meth)acryloyl moiety include the following

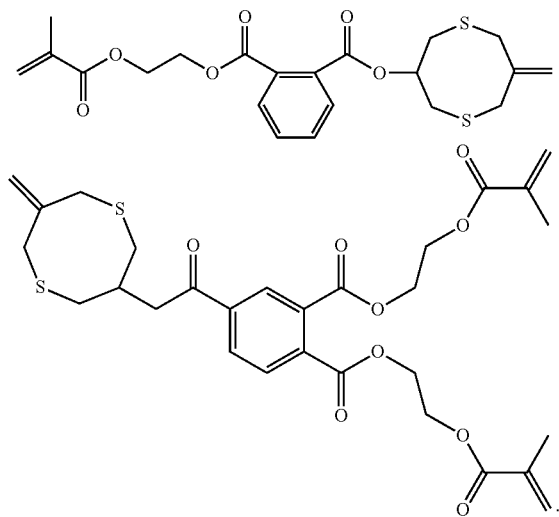

Other suitable monomers are described in US2008/0194722.

The polymerizable resin of the unfilled dental composition typically comprises at least 25 wt-% or 30 wt-% of one or more low volume shrinkage monomer, such as those previously described. In favored embodiments, the polymerizable resin of the unfilled dental composition comprises at least 35 wt-%, 40 wt-% or 45 wt-% of one or more low volume shrinkage monomer. The polymerizable resin of the unfilled dental composition typically comprises no greater than 20 wt-% or 25 wt-% of conventional (meth)acrylate monomers (such as BisGMA or urethane di(meth)acrylate). Hence, the polymerizable resin composition may comprise up to 75 wt-% or 80 wt-% of low volume shrinkage monomer(s).

In some embodiments, the polymerizable resin of the unfilled dental composition comprises at least 45 wt-% or 50 wt-% up to 60 wt-% or 65 wt-% of a multi (meth)acrylate low volume shrinkage monomer. Such monomer may be a tri(meth)acrylate monomer. The polymerizable resin may further comprises at least 10 wt-% or 15 wt-% up to 25 wt-% or 30 wt-% of a mono(meth)acrylate low volume shrinkage monomer such as the previously described monomer comprising a cyclic sulfide moiety.

The curable component of the curable dental composition can include a wide variety of other ethylenically unsaturated compounds (with or without acid functionality), epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates) such as, methyl(meth)acrylate, ethyl(meth)acrylate, isopropyl(meth)acrylate, n-hexyl(meth)acrylate, stearyl (meth)acrylate, allyl(meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups in a single molecule. Examples of such materials include hydroxyalkyl(meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (BisGMA). Suitable ethylenically unsaturated compounds are available from a wide variety of commercial sources, such as Sigma-Aldrich, St. Louis.

In some embodiments, the dental composition comprises a monomer having hydroxyl groups such as BisGMA is an amount of at least 5 wt-% and no greater than about 20 wt-% for the purpose of modifying the mechanical strength. Further, the dental composition may further comprise a monomer, such as a urethane dimethacrylate, for the purpose of adjusting the flexibility.

The dental compositions described herein may include one or more curable components in the form of ethylenically unsaturated compounds with acid functionality. Such components contain acidic groups and ethylenically unsaturated groups in a single molecule. When present, the polymerizable component optionally comprises an ethylenically unsaturated compound with acid functionality. Preferably, the acid functionality includes an oxyacid (i.e., an oxygen-containing acid) of carbon, sulfur, phosphorous, or boron.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate (e.g., HEMA) phosphates, bis((meth)acryloxyethyl) phosphate, ((meth)acryloxypropyl)phosphate, bis((meth) acryloxypropyl)phosphate, bis((meth)acryloxy)propyloxy phosphate, (meth)acryloxyhexyl phosphate, bis((meth)acryloxyhexyl)phosphate, (meth)acryloxyoctyl phosphate, bis ((meth)acryloxyoctyl)phosphate, (meth)acryloxydecyl phosphate, bis((meth)acryloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like, may be used as components. Also monomers, oligomers, and polymers of unsaturated carbonic acids such as (meth)acrylic acids, aromatic (meth)acrylated acids (e.g., methacrylated trimellitic acids), and anhydrides thereof can be used.

The dental compositions can include an ethylenically unsaturated compound with acid functionality having at least one P—OH moiety. Such compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler.

The curable dental compositions may include resin-modified glass ionmers cements such as those described in U.S. Pat. No. 5,130,347 (Mitra) U.S. Pat. No. 5,154,762 (Mitra) U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the polymerizable resin. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the composition is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

Curable dental compositions can also be cured with a thermally or heat activated free radical initiator. Typical thermal initiators include peroxides such as benzoyl peroxide and azo compounds such as azoisobutyronitrile.

In some embodiments, such as when the dental composition is employed as a dental restorative (e.g. dental filling or crown) or an orthodontic adhesive, the dental composition typically comprises appreciable amounts of (e.g. nanoparticle) filler. Such compositions typically include at least 40 wt-%, or at least 45 wt-%, or at least 50 wt-% filler, based on the total weight of the composition. In some embodiments the total amount of filler is at most 90 wt-%, or at most 80 wt-%, or at most 75 wt-% filler.

In such dental compositions comprising appreciable amounts of filler, the composition comprises (e.g. low volume shrinkage) (meth)acrylate monomers in an amount totaling at least 5 wt-%, 6 wt-%, 7 wt-%, 8 wt-%, 9 wt-%, or 10 wt-%, based on the total weight of the composition. The concentration of (e.g. multifunctional) polymerizable monomers is generally no greater than about 60 wt-%. In some embodiments the total amount of polymerizable resin is no greater than 40 wt-%, or 30 wt-%, or 25 wt-%.

Dental compositions suitable for use as dental adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some embodiments, the dental compositions can have an initial color remarkably different than the cured dental structures. Color can be imparted to the composition through the use of a photobleachable or thermochromic dye.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. Dental adhesives are also hardened by curing after applying the dental composition to the tooth. The method of treating an oral surface may comprise providing a dental article and adhering the dental article to an oral (e.g. tooth) surface. The dental article may comprise a cured composition of the hardenable dental composition described herein.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless

| | |
|---|---|
| TrisMAP | Prepared as described in Example 2, WO 2008/082881, having a calculated molecular weight of 1131 g/mole. |
| 3-isocyanatopropyltriethoxy silane | Sigma-Aldrich (St. Louis, MO) |
| Dibutyltin dilaurate | Sigma-Aldrich |
| UDMA | Diurethane dimethacrylate CAS #72869-86-4 2-Propenoic acid, 2-methyl-, 7,7,9 (or 7,9,9) trimethyl-4,13-dioxo 3,14-dioxa-5, 12-diazahexadecane-1,16-diyl ester, available from Dajac Laboratories |
| BisEMA6 (ethoxylated bisphenol A methacrylate esters) available as Sartomer CD541 | Sartomer (Union Carbide) |
| CAMP | Prepared as described in Preparative Example 2, WO 2008/082881, having a calculated molecular weight of 436 g/mole. |
| CPQ (camphorquinone) | Sigma-Aldrich |
| EDMAB (ethyl 4-(N,N-dimethylamino)benzoate) | Sigma-Aldrich |
| DPIHFP | Diphenyl Iodonium Hexafluorophosphate (Alpha Aesar, Ward Hill, MA) |
| BZT (benzotriazole) | Sigma-Aldrich |
| BHT (butylated hydroxytoluene) | Sigma-Aldrich |
| Silica-zirconia Cluster Filler | Prepared as described in Preparative Example A, US 6730156 |
| GF-31 (3-methacryloxypropyltrimethoxy silane), available as Geniosil GF-31 | Wacker Chemie, Germany |
| 20 nm silica particles (surface treated) | Prepared as described for Filler F, US 2005/0252413 |
| BisGMA (2,2-bis[4-(2-hydroxy-3-methacryloxypropoxy)phenyl]propane) | Sigma-Aldrich |

Preparation of 1,2-Bis(2-Methacryloyloxyethyl)-4-(7-methylene-1,5-dithiaoctan-3-yl)trimellitate [TCAM-DiHEMA] (Also Described in Abuelyaman et al WO 2006/122081 A1)

Trimillitic acid (21.0 g, 0.10 mol TCI) was suspended in 200 ml of acetone in a 500 ml 3-neck flask equipped with a mechanical stirrer, a thermocouple connected to a temperature controller, a dry air stream running through a T-shape connection into the reactor then to an oil bubbler, and an ice bath. Then added were C-8 alcohol (17.6 g, 0.1 mol), HEMA (26.2 g, 0.2 mol), 4-(dimethylamino)pyridine (DMAP, 4 g, 0.03 mol, CAS #1122-58-3, Alfa Aesar, lot L125009) and BHT (60 mg). The mixture was cooled in the ice bath for 15-20 minutes (thermocouple reading was 0-5° C.). A solution of DCC (62.5 g, 0.303 mol) dissolved in 100 ml acetone was placed into a 500 ml dropping funnel which was placed in-between the reaction flask and the dry air in-let. The DCC solution was added drop-wise to the cold and vigorously stirred mixture in a manner that the temperature didn't exceed 10° C. After complete addition of the DCC solution, the flask was kept in the ice bath for 2 hours then at room temperature overnight.

On the second day, the solid formed was removed by filtration followed by concentrating the filtrate using a rotary evaporator. The residue was dissolved in 300 ml 2:1 ethylacetate:hexane then extracted with 100 ml of each of 1.0 N. HCl, 10% aqueous NaHCO$_3$, H$_2$O, and brine. The organic layer was dried by Na$_2$SO$_4$ then concentrated and dried using a rotary evaporator to give 57 g (96.6% yield) of a light yellow oil.

Preparation of THPICTHP

A sample of HEMA phthalate made according to the procedure described above for THEICTHP was purified from the DMAP catalyst by dissolving in ethylacetate/hexanes 2:1 then extracting with 1.N HCl then washing with water followed by brine. The acid was concentrated then used in making THPICTHP.

HEMA-phthalate (135 g, 0.486 mol) was charged into a 250 ml 3-neck flask equipped with a mechanical stirrer, a thermocouple connected to a temperature controller, a dry air stream running through a T-shape connection into the reactor then to an oil bubbler, and a heating mantle. Triphenylantimony (1.4 g) was added and the mixture was heated to 100° C. Tris-epoxypropyl isocyanurate (57.15 g, 0.172 mol) was added in small increments over 1 hour. After complete addition, heating at 100 was resumed for 4 hours. Triphenylphosphine (0.360 g) was added and heating at 100 was continued for another 3 hours. The heat was turned off and the obtained viscous liquid was collected in quantitative yield.

Refractive index was measured and found to be 1.5365. By use of NMR the liquid was determined to be the product shown is the following reaction scheme. The calculated molecular weight of the depicted end product was determined to be 1131 g/mole. The calculated molecular weight of the linking group was determined to be 250 g/mole.

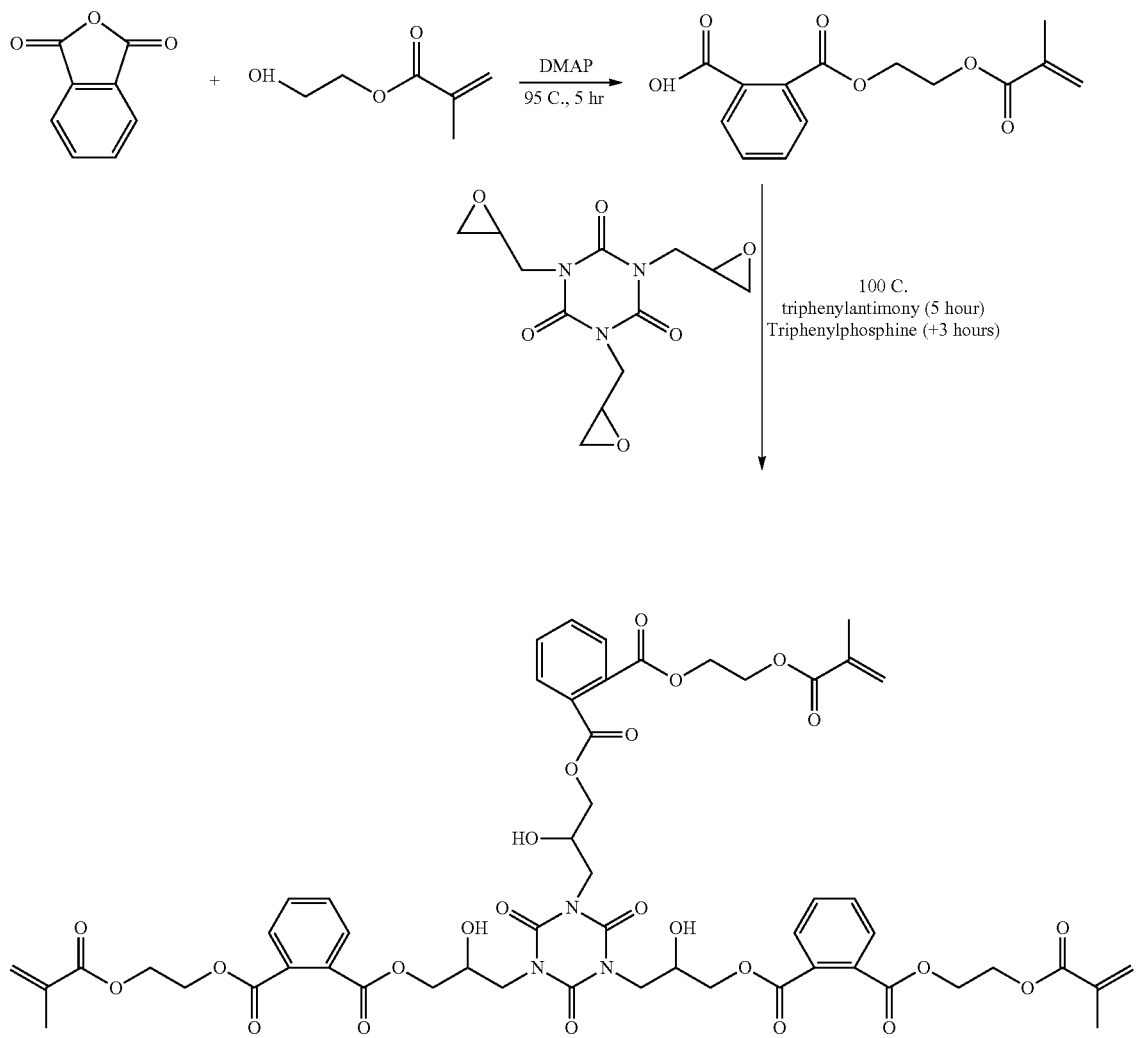

Synthesis of Tri-HydroxyEthyl Iso Cyanurate Di-HEMA Phthalate (THEICDHP)

THEICDHP was made from tris-(2-hydroxyethyl)isocyanurate (26.6 g, 0.10 mole) and 2 equivalents of mono-(2-methacryloxyethyl)phthalate (56.6 g, 0.20 mol) following the same procedure described for THEICTHP above. The product was isolated as a viscous liquid and structure was confirmed by NMR. The calculated molecular weight of the depicted end product was determined to be 781 g/mole. The calculated molecular weight of the linking group was determined to be 220 g/mole.

curing box (Heraeus Kulzer GmbH, Germany). Cured samples were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Five cylinders of cured samples were prepared and measured with the results reported in MPa as the average of the five measurements.

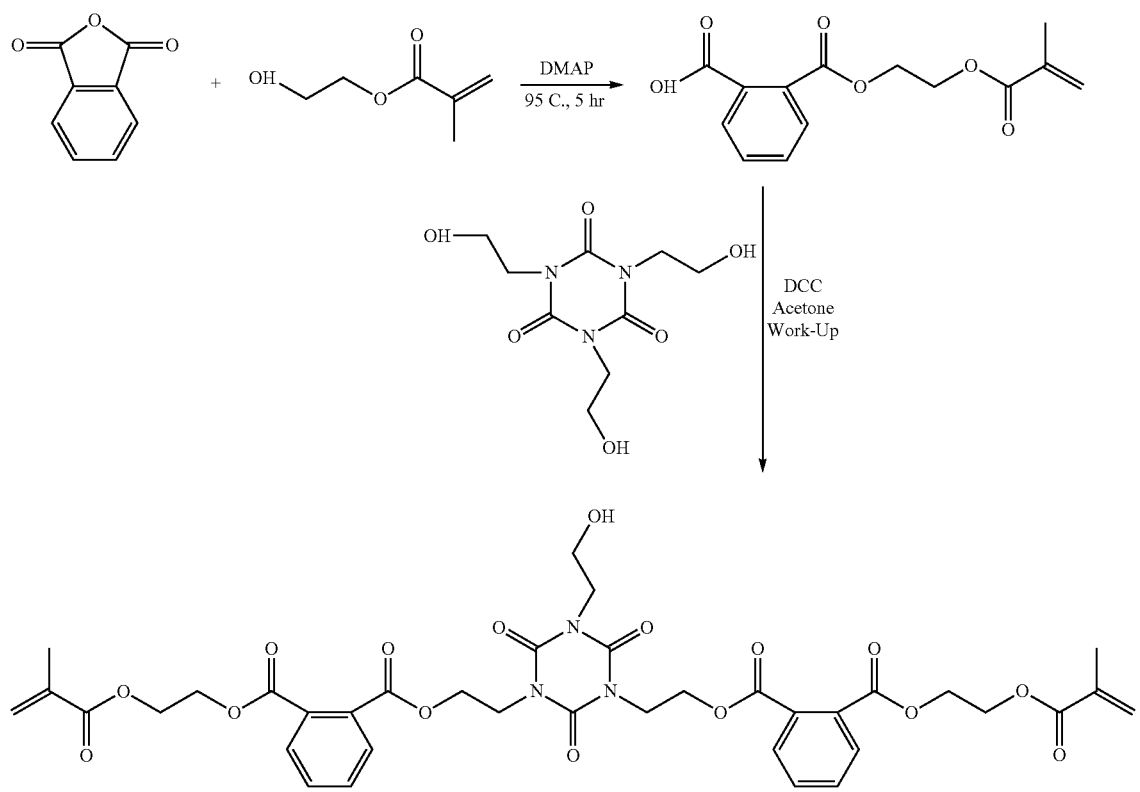

Test Methods:

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three to five replicates for each sample.

Diametral Tensile Strength (DTS) Test Method

DTS of a test sample was prepared according to the following procedure. An uncured sample was injected into a 4-mm (inside diameter) glass tube that was capped with silicone rubber plugs; and then the tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS

Preparation of Silane Surface Treatment Compounds

1. Preparation of TrisMAP Silane 31.242 g of TrisMAP was dissolved into 41.270 g of dry ethyl acetate, and 10.012 g of 3-isocyanatopropyltriethoxy silane was added to the mixture. 1 drop of dibutyl tin dilaurate was then added. The material was allowed to react with stirring in a sealed vessel for 72 hours. The disappearance of the isocyanate peak at approximately 2300 cm$^{-1}$ was noted by infrared spectroscopy to confirm the reaction between the isocyanate group and the alcohol. The calculated molecular weight was 1378 g/mole.

2. Preparation of BisGMA silane 20.330 g BisGMA were reacted with 19.650 g 3-isocyanatopropyltriethoxysilane, and stirred to dissolve for 2 hours. 2 drops of dibutyltin dilaurate were added to catalyze the reaction and was let stir to react. The calculated molecular weight was 1007 g/mole.

3. Preparation of THPICTHP silane 4.849 g of the THPICTHP resin (synthesized as described above) was mixed with 1.65 g of 3-isocyanatopropyl triethoxysilane, and 6.435 g of dry ethyl acetate and dissolved. To this, 1 drop of dibutyltin dilaurate was added to catalyze the reaction, and was allowed to react at room temperature overnight. A 50% solution was obtained. The calculated molecular weight was 1514 g/mole.

4. Preparation THEICDHP silane 5.0407 g of the THEICDHP resin (synthesized as described above) was mixed with 1.5978 g 3-iscocyanatopropyltriethoxysilane and 6.656 g dry ethyl acetate and stirred to dissolve. To this 1 drop of dibutyltin diluarate was added to catalyze the reaction, and was allowed to react at room temperature overnight. A 50% solution was obtained.

The calculated molecular weight was 1028 g/mole.

Preparation of Surface-Treated Silica-Zirconia Cluster Fillers 1. 25 g of silica/zirconia cluster was mixed with BisGMA silane, and 25.964 g ethyl acetate and 0.440 g 30% NH4OH solution and stirred to react overnight at room temperature. This slurry was then flash dried in the hood, and heated to 80 C/30 min to finish the reaction.

2. 25.038 g silica/zirconia cluster was mixed with 5.238 g of the 50% THPICTHP silane solution above, and with 27.18 g ethyl acetate and 0.1457 g 30% NH4OH solution and stirred to react overnight at room temperature. This slurry was then flash dried in the hood, and heated to 80 C/30 min to finish the reaction.

3. 25.00 g silica/zirconia cluster was mixed with 5.262 g of the 50% THEICDHP silane solution above, and with 25.2 g ethyl acetate and 0.52 g 30% NH4OH solution and stirred to react overnight at room temperature. This slurry was then flash dried in the hood, and heated to 80 C/30 min to finish the reaction.

The silica zirconia cluster fillers were surface treated with GF-31 (as a comparative), TrisMAP silane, and mixtures of TrisMAP Silane and GF-31 by weighing approximately equal weights of ethyl acetate and silica-zirconia cluster filler, adding the silane surface treatment compound solution(s) at an appropriate amount to provide the target % weight of silane on the filler, and were catalyzed by the addition of 1.75% (by weight of the filler) 30% ammonium hydroxide solution. The combination of surface treatment compound and filler were allowed to react at room temperature for a minimum of 16 hours, flashed dried in a solvent hood to remove the ethyl acetate, and then heated between 80-90° C. for 30 minutes to finish any condensation reaction.

Preparation of Dental Composite Composition

The surface treated silica-zirconia cluster fillers were combined with the following low volume shrinkage polymerizable resin compositions, having the concentrations of components described as follows and mixed until uniform.

Resin 1:

| Component | wt % |
| --- | --- |
| TrisMAP: | 57.1% |
| UDMA: | 8.5% |
| BisEMA-6: | 12.1% |
| CAMP: | 19.4% |
| CPQ | 0.23% |
| EDMAB | 1.0% |
| BZT | 1.5% |
| BHT: | 0.15% |

Resin 2:

| Component | wt % |
| --- | --- |
| TrisMAP: | 57.7% |
| UDMA: | 8.6% |
| BisEMA-6: | 12.3% |
| CAMP: | 19.6% |
| CPQ | 0.23% |
| EDMAB | 1.0% |
| DPIHPF | 0.5% |
| BHT: | 0.15% |

Resin 3:

| Component | wt % |
| --- | --- |
| TrisMAP: | 57.7 % |
| UDMA: | 8.6 % |
| BisEMA-6: | 12.3 % |
| TCAMdiHEMA: | 19.6 % |
| CPQ | 0.23 % |
| EDMAB | 1.0 % |
| DPIHPF | 0.5 % |
| BHT: | 0.15 % |

| Paste | Resin 1 | Cluster filler w/BisGMA silane | Cluster filler w/GF-31 | 20 nm Treated Silica (wt %) | Watts Shrinkage (%) | Watts Shrinkage Difference (Control − Example) |
| --- | --- | --- | --- | --- | --- | --- |
| Example 1 | 27.04 | 66.01 | | 6.95 | −1.39 | −0.21 |
| Control A | 27.01 | | 66.03 | 6.94 | −1.61 | |

The results show that the use of the BisGMA silane surface treatment compound resulted in a reduction in shrinkage in comparison to the GF-31 silane surface treatment compound.

| Paste | Resin 2 | Resin 3 | Cluster filler w/ GF-31 | Cluster filler w/ THPICTHP silane | Cluster filler w/ THEICDHP silane | 20 nm Treated Silica (wt %) | Watts Shrinkage (%) | Watts Shrinkage Difference (Control – Example) |
|---|---|---|---|---|---|---|---|---|
| Ex. 2 | 27 | | | 66.06 | | 6.93 | −1.71 | −0.09 |
| Control B | 27 | | 66.06 | | | 6.94 | −1.80 | |
| Ex. 3 | 25.5 | | | | 67.42 | 7.07 | −1.55 | −0.10 |
| Control C | 25.5 | | 67.42 | | | 7.08 | −1.65 | |
| Ex. 4 | | 30 | | | 63 | 7 | −1.65 | −0.22 |
| Control D | | 30 | 63 | | | 7 | −1.87 | |

The results show that the use of the THPICTHP silane and THEICDHP silane surface treatment compound both resulted in a reduction in shrinkage in comparison to the GF-31 silane surface treatment compound.

| Paste | Resin 1 | Cluster filler w/ TrisMAP Silane | Cluster filler w/50/50 TrisMAP/GF-31 Silanes | Cluster filler w/75/25 TrisMAP/GF-31 Silanes | Cluster filler w/90/10 TrisMAP/GF-31 Silanes | Cluster filler GF-31 | 20 nm Treated Silica (wt %) | Watts Shrinkage (%) | Watts Shrinkage Difference (Control – Example) |
|---|---|---|---|---|---|---|---|---|---|
| Control E | 27 | | | | | 66.07 | 6.94 | −1.51 | |
| Ex. 5 | 27 | | 66.07 | | | | 6.94 | −1.47 | −0.04 |
| Ex. 6 | 27 | | | 66.07 | | | 6.94 | −1.39 | −0.12 |
| Ex. 7 | 27 | | | | 66.07 | | 6.94 | −1.41 | −0.10 |
| Ex. 8 | 25 | | | 67.88 | | | 7.13 | −1.32 | −0.19 |
| Ex. 9 | 25 | 67.88 | | | | | 7.13 | −1.29 | −0.22 |

The results show that the use of the TrisMAP silane surface treatment compound and combinations of the TrisMAP silane with the GF-31 silane resulted in a reduction in shrinkage in comparison to solely GF-31 silane surface treatment compound.

| Paste | Resin 1 | Cluster filler w/ TrisMAP Silane | Cluster filler w/50/50 TrisMAP/GF-31 Silanes | Cluster filler w/75/25 TrisMAP/GF-31 Silanes | Cluster filler w/90/10 TrisMAP/GF-31 Silanes | Cluster filler GF-31 | 20 nm Treated Silica (wt %) | Watts Shrinkage (%) | Watts Shrinkage Difference (Control – Example) |
|---|---|---|---|---|---|---|---|---|---|
| Control F | 27 | | | | | 66.07 | 6.94 | −1.51 | |
| Ex. 5 | 27 | | 66.07 | | | | 6.94 | −1.47 | −0.04 |
| Ex. 6 | 27 | | | 66.07 | | | 6.94 | −1.39 | −0.12 |
| Ex. 7 | 27 | | | | 66.07 | | 6.94 | −1.41 | −0.10 |
| Ex. 8 | 25 | | | 67.88 | | | 7.13 | −1.32 | −0.19 |
| Ex. 9 | 25 | 67.88 | | | | | 7.13 | −1.29 | −0.22 |

The Diametral Tensile Strength of Examples 5, 6, 7 and 10 were measured as follows:

| Paste | Diametral Tensile Strength |
|---|---|
| Ex. 5 | 68.55 |
| Ex. 6 | 66.81 |
| Ex. 7 | 57.60 |

| Paste | Resin 1 | Cluster filler w/ TrisMAP Silane | Cluster filler w/ GF-31 Silane | 20 nm Treated Silica (wt-%) | Watts Shrinkage Difference (Control – Example) | Diametral Tensile Strength (MPa) |
|---|---|---|---|---|---|---|
| Ex. 10 | 27 | 66.07 | | 6.94 | −0.31 | 65.20 (3.85) |
| Control G | 27 | | 66.07 | 6.94 | | 71.93 (3.85) |

What is claimed is:

1. A method of surface treating inorganic oxide particles comprising: forming a surface treatment compound by reacting a first functional group of a (meth)acrylate monomer having a molecular weight of at least 350 g/mole with a second functional group of a silane compound wherein the first and second functional groups are not free-radically polymerizable groups and react to form a covalent bond; and combining the surface treatment compound with inorganic oxide particles.

2. The method of claim 1 wherein the method is sequential comprising first preparing the surface treatment compound followed by combining the surface treatment compound with the inorganic oxide particles.

3. The method of claim 1 wherein the covalent bond forms a urethane, urea, or amide linkage.

4. The method of claim 1 wherein the surface treatment compound has a molecular weight of at least 600 g/mole.

5. The method of claim 1 wherein the (meth)acrylate monomer has a refractive index of at least 1.50.

6. The method of claim 1 wherein the (meth)acrylate monomer is branched or comprises a cyclic moiety.

7. The method of claim 1 wherein the (meth)acrylate monomer is a multi(meth)acrylate monomer.

8. The method of claim 7 wherein the (meth)acrylate monomer is a multi(meth)acrylate comprises at least three (meth)acrylate groups.

9. The method of claim 1 wherein the (meth)acrylate monomer has the formula

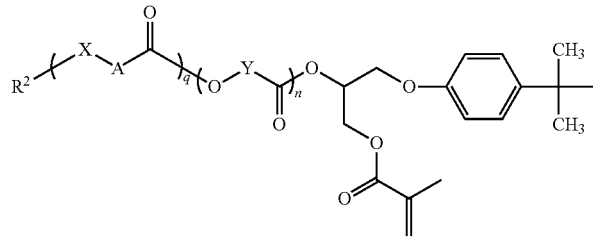

wherein each X independently represents an oxygen atom (O) or a nitrogen atom (N); Y and A each independently represent an organic group, m=1 to 5; n=0 to 5; p and q are independently 0 or 1; and $R^1$ and $R^2$ each independently represent H, —C(O)CH=CH$_2$, or —C(O)C(CH$_3$)=CH$_2$; wherein at least one of $R^1$ and $R^2$ is H or at least one Y, A, or X when X is nitrogen comprises the first functional group that reacts to form the covalent bonds with the second functional group of the silane compound.

10. The method of claim 1 wherein the (meth)acrylate monomer is an isocyanurate monomer.

11. The method of claim 10 wherein the (meth)acrylate monomer has the general structure

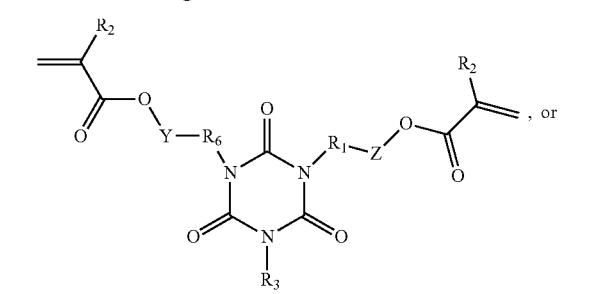

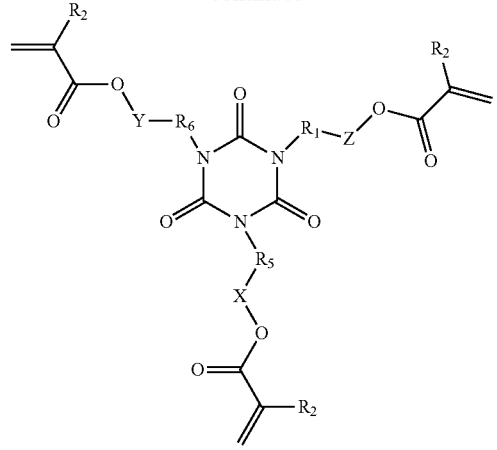

wherein $R_1$, $R_5$, and $R_6$ are independently alkylene, arylene, or alkarylene, optionally including a heteroatom;

X, Y, and Z are independently alkylene, arylene, or alkarylene linking groups, comprising a heteroatom;

$R_3$ is independently hydrogen, alkyl, aryl, or alkaryl, optionally including a heteroatom; and $R_2$ is hydrogen or methyl;

wherein at least one of $R_1$, $R_3$, $R_5$, $R_6$, X, Y, and Z comprises the first functional group that reacts to form the covalently bonds with a second functional group of the silane compound.

12. The method of claim 11 wherein X, Y, and Z comprise at least one moiety selected from ester, thioester, ether, thioether, or combinations of such moieties.

13. The method of claim 1 wherein the surface treatment further comprises a non-polymerizable silane surface treatment compound.

14. The method of claim 1 wherein the inorganic oxide particles comprises silica, zirconia, or a mixture thereof.

15. The method of claim 1 wherein the inorganic oxide particles comprise nanoparticles.

16. The method of claim 1 wherein the inorganic oxide particles comprise nanoclusters.

17. The method of claim 1 wherein the surface treatment compound is combined with the inorganic oxide particles in a solvent.

18. The method of claim 1 further comprising drying the surface treated inorganic oxide particles to a free-flowing powder.

* * * * *

UNITED STATES PATENT AND TRADEMARK OFFICE
CERTIFICATE OF CORRECTION

PATENT NO.        : 9,050,252 B2
APPLICATION NO.   : 13/695443
DATED             : June 9, 2015
INVENTOR(S)       : Bradley Craig Page 1 of 2

It is certified that error appears in the above-identified patent and that said Letters Patent is hereby corrected as shown below:

In the Specification

Column 1
Line 23, Delete "wt-%" and insert -- 25 wt-% --, therefor.

Column 4
Line 45, Delete "moities)" and insert -- moieties) --, therefor.

Column 6
Line 26, Delete "3-isocyantopropyltriethoxy" and insert -- 3-isocyanatopropyltriethoxy --, therefor.

Column 9
Line 29-42,

Delete " 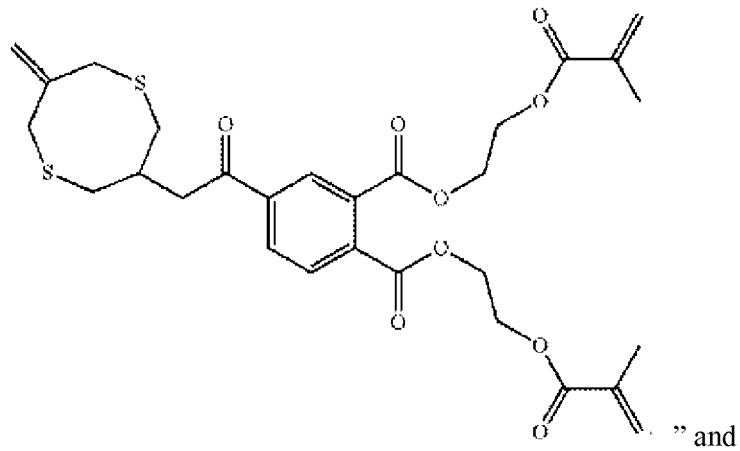 " and

Signed and Sealed this
Fifteenth Day of March, 2016

Michelle K. Lee
*Director of the United States Patent and Trademark Office* insert -- 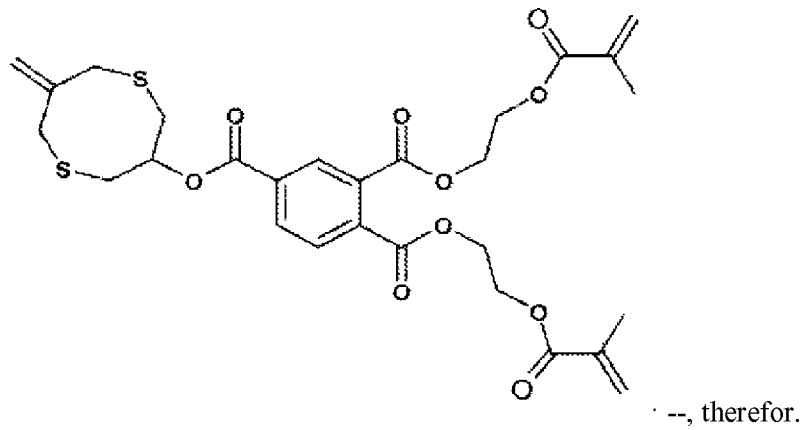 --, therefor.

Column 10
Line 28, Delete "bisphenolA" and insert -- bisphenol A --, therefor.
Line 48-49, Delete "ethacryloxypropoxy" and insert -- methacryloxypropoxy --, therefor.

Column 11
Line 49, Delete "ionmers" and insert -- ionomers --, therefor.

Column 12
Line 12, Delete "tetrafluoroboarate." and insert -- tetrafluoroborate. --, therefor.

Column 18
Line 7, After "Unless" insert -- otherwise indicated, all parts and percentages are on a weight basis. --.
Line 30, Delete "(Alpha Aesar," and insert -- (Alfa Aesar, --, therefor.
Line 50, Delete "Trimillitic" and insert -- Trimellitic --, therefor.

Column 19-20
Line 19, Delete "95 C.," and insert -- 95° C., --, therefor.
Line 20, Delete "100 C.," and insert -- 100° C., --, therefor.

Column 21-22
Line 13, Delete "95 C.," and insert -- 95° C., --, therefor.

Column 23
Line 15-16, Delete "3-iscocyanatopropyltriethoxysilane" and insert
-- 3-isocyanatopropyltriethoxysilane --, therefor.
Line 17, Delete "diluarate" and insert -- dilaurate --, therefor.

In the Claims

Column 27
Line 49, In Claim 9, delete "bonds" and insert -- bond --, therefor.

Column 28
Line 44, In Claim 11, delete "covalently bonds" and insert -- covalent bond --, therefor.